US006258940B1

(12) United States Patent
Kabyemela et al.

(10) Patent No.: US 6,258,940 B1
(45) Date of Patent: Jul. 10, 2001

(54) METHOD FOR PRODUCING ERYTHROSE

(75) Inventors: Bernard M. Kabyemela; Tadafumi Adschiri; Kunio Arai, all of Miyagi-ken (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 08/960,367

(22) Filed: Oct. 29, 1997

(30) Foreign Application Priority Data

Apr. 30, 1997 (JP) ..................................... 9-112820

(51) Int. Cl.⁷ .............................. C07H 15/00; C07G 3/00
(52) U.S. Cl. ............................................ 536/18.5; 536/4.1
(58) Field of Search ..................................... 536/4.1, 18.5

(56) References Cited

FOREIGN PATENT DOCUMENTS

07095900 * 4/1995 (JP) ................................ C13K/1/02

OTHER PUBLICATIONS

Adschiri et al., Industrial Eng. Chemistry Research, vol. 35, No. 5, pp. 1552–1558, (abstract), May, 1997.*

American Institute of Chemical Engineers 1996 Annual Meeting; Bernard M. Kabyemela; "Reaction Pathway of Glucose and Fructose in Subcritical and Supercritical Water"; Nov. 10–15, 1996.

* cited by examiner

*Primary Examiner*—James O. Wilson
(74) *Attorney, Agent, or Firm*—Oblon, Spivak, McClelland, Maier & Neustadt, P.C.

(57) ABSTRACT

A method for producing erythrose, comprising subjecting glucose to a decomposition reaction using water at a supercritical state or at a sub-critical state as the solvent therefor, and a method for producing erythrose from glucose, wherein the reaction time is set to a time period suitable for a high production level of erythrose and a low level of contaminated by-products.

16 Claims, 4 Drawing Sheets

METHOD FOR PRODUCING ERYTHROSE

BACKGROUND OF THE INVENTION

1. Field of the Invention

Erythrose has a great number of applications in the fields of foods, polymers, fine chemicals, the medicinal industry, and the like. Erythritol produced by reducing erythrose is currently utilized as a low calorie sweetener.

2. Discussion of the Background

As to processes for preparing erythrose, the method by Wohl is known, which comprises decomposing D-arabinose oxime by way of acetylated aldononitrile (Wohl, A., Ber., Vol. 65, 168, 1893), but the yield of erythrose by this method is low. Additionally, another method comprising glucose oxidation using lead tetraacetate is known (Whistler R. L., et. al., Methods in Carbohydrate Research, Academic Press, Vol. 1, 64–66, 1962). The method, however, requires multiple complex steps, and therefore, the method is hardly applicable to an industrial process, although the method is indeed effective as a method for preparing erythrose in laboratories.

Alternatively, it has been known that cellulose can be decomposed into water-soluble products such as glucose through a decomposition reaction where water in a super-critical state or in a sub-critical state is used as the solvent, and that in such decomposition reaction various by-products such as erythrose, fructose and glyceraldehyde are produced ("Science and Technology of Super-critical Fluid", Sankyo Business, 280–286, 1996). However, the yield of erythrose produced through these reactions is low, and therefore, these methods cannot be substantially applied to the preparation of erythrose.

SUMMARY OF THE INVENTION

It is one object of the present invention to provide an efficient and simple method for preparing erythrose.

So as to attain the object described above, the present inventors have discovered that erythrose can selectively be produced by subjecting glucose to a decomposition reaction using water in a super-critical state or in a sub-critical state as the solvent, and that highly pure erythrose products can be obtained in high yields under specific conditions for the reaction period. The present invention has been completed on the basis of these findings.

More specifically, the present invention relates to a method for producing erythrose, comprising subjecting glucose to a decomposition reaction using water in a super-critical state or in a sub-critical state as the solvent therefor, and also to such method for producing erythrose from glucose, wherein the reaction time is set to such a time period that erythrose can be produced at a high level, whereas by-products are produced at low levels.

DETAILED DESCRIPTION OF THE INVENTION

Figure 1:
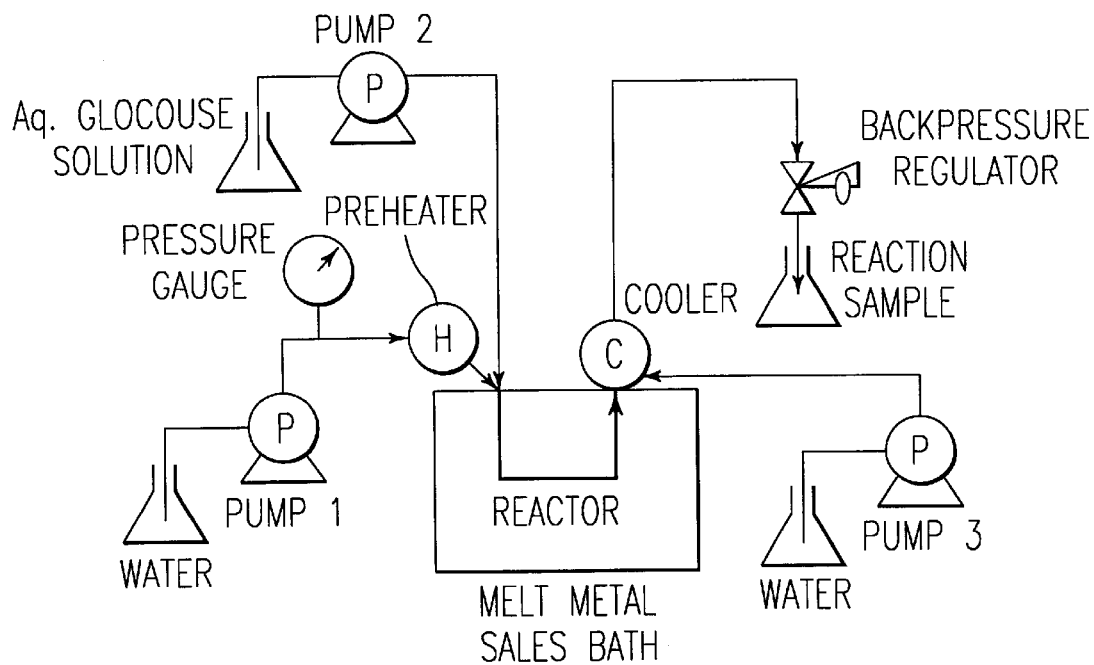
FIG. 1 is a schematic view depicting an example of a system arranged to carry out the present invention.

In accordance with the present invention, the subjection of glucose to a decomposition reaction using water at a super-critical state or at a sub-critical state as the solvent means more specifically the putting of an aqueous solution of glucose in a super-critical state or a sub-critical state. Such super-critical state or sub-critical state is a state existing within a temperature range of 200 to 800° C. and a pressure range of 2 to 90 MPa.

The concentration of glucose to be used as the raw material should preferably be within a range where it is dissolvable in the solvent water, and preferably, the concentration is 0.1 to 10% by weight from the viewpoint of reaction efficiency.

Furthermore, the period of the decomposition reaction, namely the period to maintain an aqueous solution of glucose at the above-mentioned super-critical or sub-critical state, is the period during which the erythrose generated from glucose is present in the reaction solution. Preferably, the period is such that the erythrose shows a high accumulation level, whereas byproducts are at low levels. Such times typically are from 0.001 to 3 sec., more preferably 0.05–0.5 sec. In Example I described below, herein, the period is 0.075 to 0.3 seconds.

In the method for producing erythrose from glucose in accordance with the present invention, a person skilled in the art is capable of choosing an appropriate decomposition reaction period by observing the time-wise ups and downs of the substances concerned, i.e., the vanishment by decomposition of the raw material glucose and the production of the objective substance erythrose and undesired by-products in the course of the decomposition reaction, by preliminary experiments. In the reaction of water at a super-critical state or at a sub-critical state with glucose in accordance with the present invention, glucose is rapidly decreased while erythrose is prominently generated, and by-product fructose is generated at the initial reaction stage (a stage where the glucose remains unreacted in an amount of 50% or more). At the intermediate reaction stage (a stage where the glucose remains unreacted in an amount of 10 to 50%), the unreacted glucose still remains, and therefore, the amount of the erythrose generated is further increased, but the amount of the fructose generated is decreased although the unreacted glucose still remains. To the inventors' surprise, at the last reaction stage (a stage where the glucose remains unreacted in an amount of 10% or less), the fructose is almost vanished, but the decrement of the erythrose is extremely small and the erythrose still remains in a significant amount in the reaction solution. Thus, and so as to prepare erythrose in high purity and in high yield, it is understood that it is very important to select an appropriate reaction time period.

Advantageously, the resultant reaction solution containing erythrose contains no solvent except water, and by-products at lower levels, so that the erythrose can be purified with no specific post-treatment of the resultant reaction solution. Purification may satisfactorily be carried out, e.g., according to usual purification processes of monosaccharides known to those of skill in this art, including for example purification with ion exchange resins.

EXAMPLES

The present invention will now be described in detail with reference to the following examples, but the invention is not limited to the examples. Without departing from the spirit of the invention as described above and below, the modification and variation of the invention is encompassed in the technical scope of the present invention.

Example 1

FIG. 1 is a schematic explanatory view of an example of a system arranged to carry out the present invention.

An aqueous solution having glucose dissolved therein in an amount of about 0.6% by weight was transferred through a conduit into a reactor at a rate of 5 ml/min using a high-pressure pump 2. Water previously heated with a pre-heater was fed through another conduit at a rate of 20 ml/min, which was mixed with the aqueous solution of glucose (the resulting mixture solution having a glucose concentration of 0.12% by weight) immediately before the water was charged into the reactor. After mixing, heating and pressurizing to a designated temperature and pressure was rapidly done to initiate the reaction. So as to confirm the reaction temperature, the temperature was measured with a chromel-alumel thermocouple immediately after the mixing point. The pressure measured with a pressure gauge mounted downstream pump 1 was assumed as the inner system pressure.

The reactor was of stainless steel and in a cylindrical form, with an inner diameter of 0.77 mm. The reactor was wholly placed in a bath of melt metal salts of $KNO_3$ and $KNO_2$, and was then preset to a designated reaction temperature. Cooling water was charged into the conduit at a rate of 14 ml/min at the reactor outlet, and simultaneously, the reaction solution was cooled with a cooler, whereby the reaction was terminated, followed by recovery of samples of the reaction solution by means of a sampler.

Through such rapid heating and rapid cooling, the amount of a sample during the reaction can be calculated on the basis of the length of the reactor. The retention time of the reaction solution or the reaction time can accurately be calculated on the basis of the flow rates and specific gravities of the aqueous glucose solution and the water. The reaction time can be modified by modifying the length of the reactor. Additionally, by using a pressure retaining valve, the pressure in the system was adjusted at a sampling point.

The glucose, fructose and erythrose in a sample were analyzed by using high-performance liquid chromatography (column; Shodex Ionpak KS 801, manufactured by Showa Denko, K. K., column temperature; 80° C., eluent; water, flow rate; 1 ml/min, and detection; differential refractive index detector). Substances with close peaks by high-performance chromatography were identified and determined by an internal standard method by adding a standard solution to the sample.

Experiments were carried out under reaction conditions at a super-critical state of 400° C. and 30 MPa for various reaction times. The results are shown in FIGS. 2A and 2B.

Figure 2A:
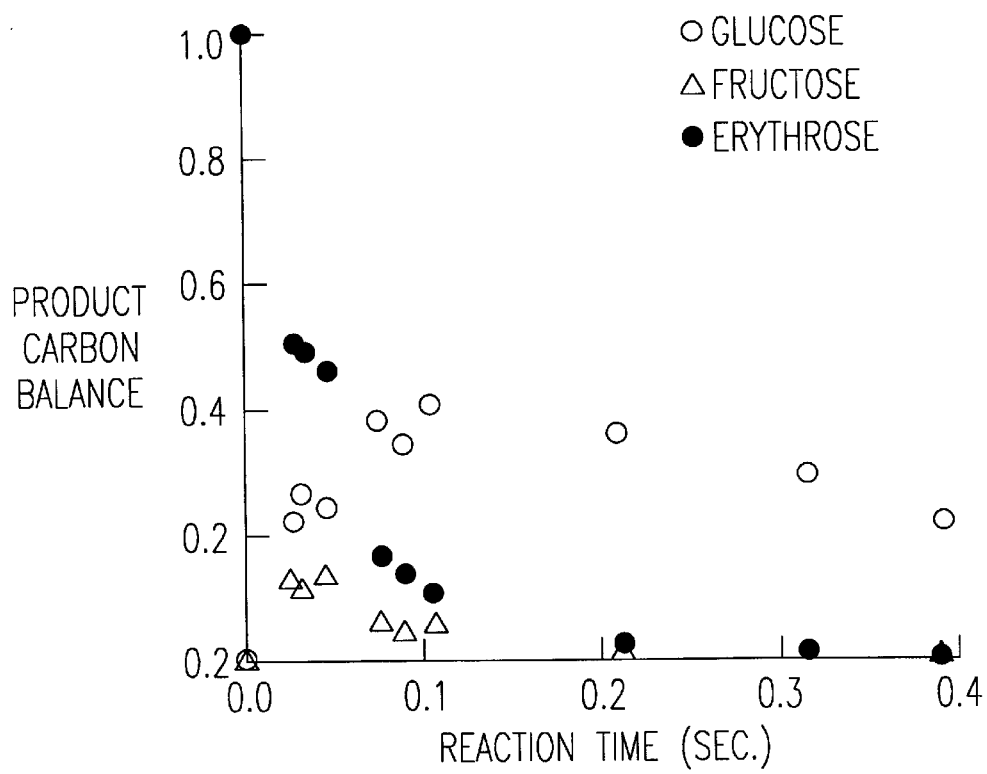
FIG. 2A is a graph showing the relation between the reaction time and the carbon weight ratios among the remaining glucose and the products (i.e., product carbon balance) (Example 1).
Figure 2B:
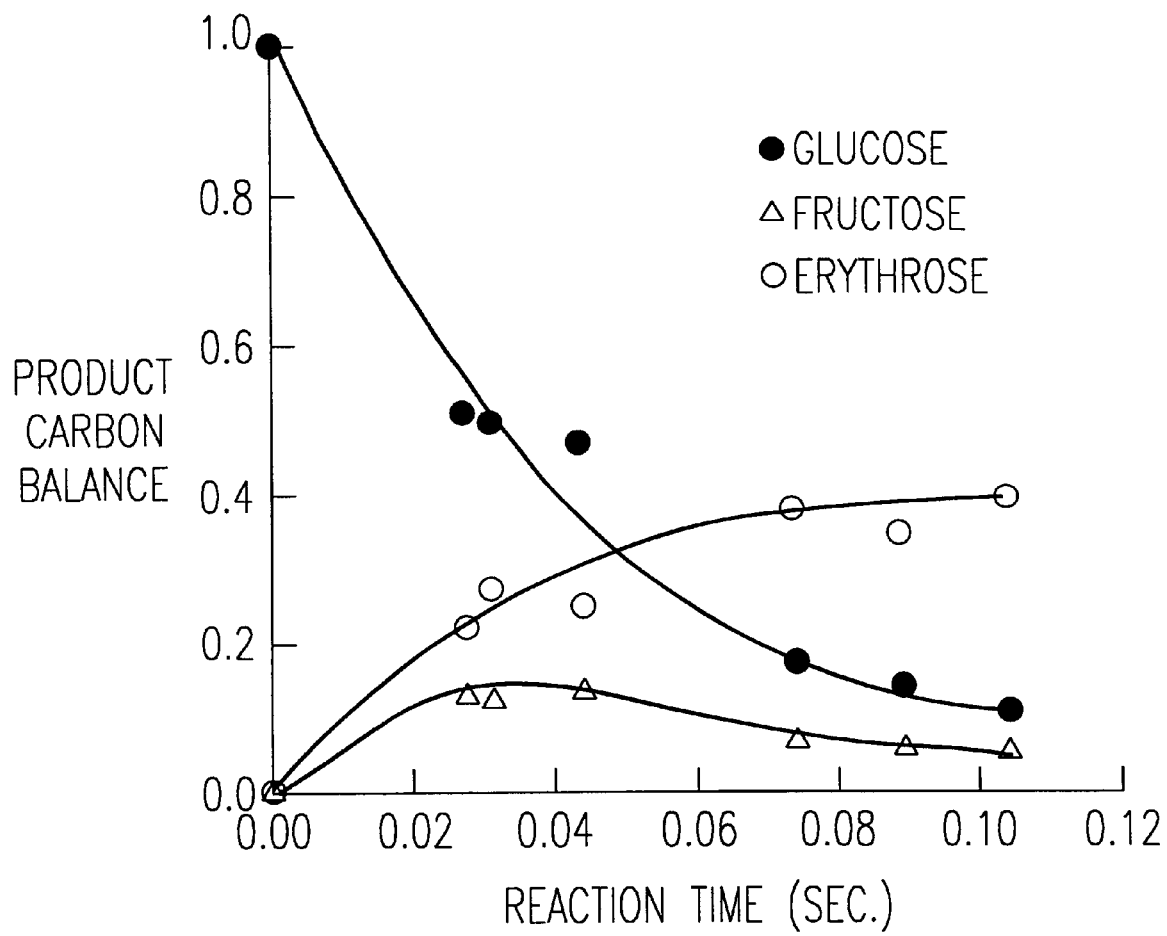
FIG. 2B is an enlarged view of the main part of FIG. 2A.

FIG. 2B is an enlarged view of a part with a short reaction time in FIG. 2A. These figures indicate that the remaining glucose concentration in the sample was decreased, involving the increase of the erythrose concentration, as the reaction time was longer; and that the erythrose concentration was about 40% of the glucose prior to the initiation of the reaction, in carbon weight ratio (i.e., product carbon balance), for a reaction time of 0.075 to 0.15 seconds, i.e., at a reaction time of 0.075 to 0.15 seconds after the initiation of the reaction. When the reaction time was shorter than 0.075 seconds, glucose was not sufficiently decomposed while fructose was produced as a by-product. Thus, the erythrose concentration (accumulation degree) was not sufficiently high. When the reaction time was 0.075 to 0.15 seconds, the molar yield of the erythrose based on the consumed glucose was about 70 molar %, which means a very high yield and a very high product selectivity. When the reaction time was 0.15 seconds or more, the glucose and the fructose were both almost totally decomposed, with almost no remaining amounts thereof in the reaction solution. The amount of the erythrose decomposed was so small that the erythrose could be recovered from the reaction solution at a high purity state.

It was confirmed by comparison of $^1H$ NMR of a freezed-dried sample with that of an erythrose standard reagent that the generated substance was erythrose.

Example 2

Figure 3A:
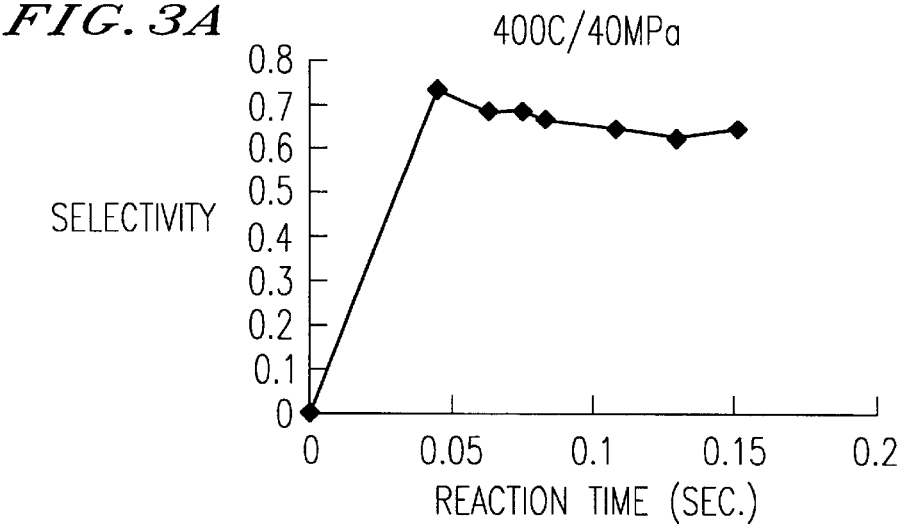
FIGS. 3A, 3B and 3C are graphs depicting the relation between the selectivity of erythrose and the reaction time at a super-critical state (Example 2).
Figure 3B:
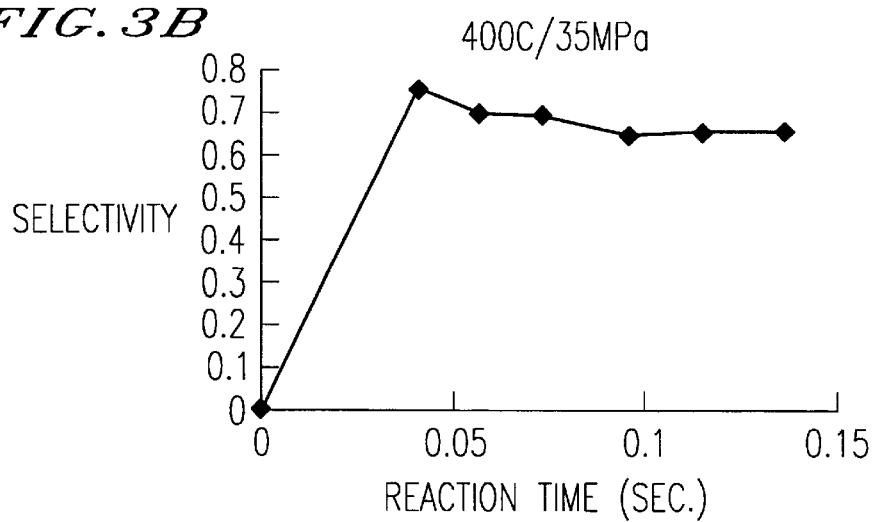
Figure 3C:
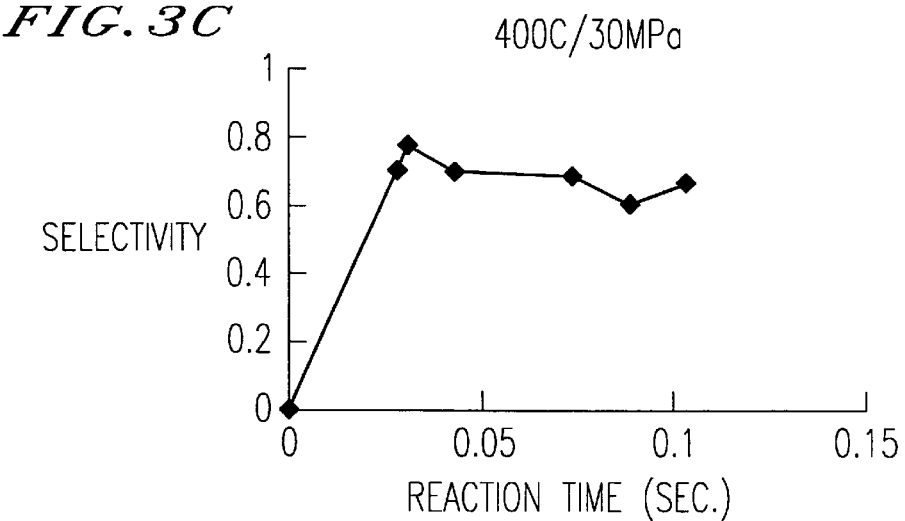
Figure 3D:
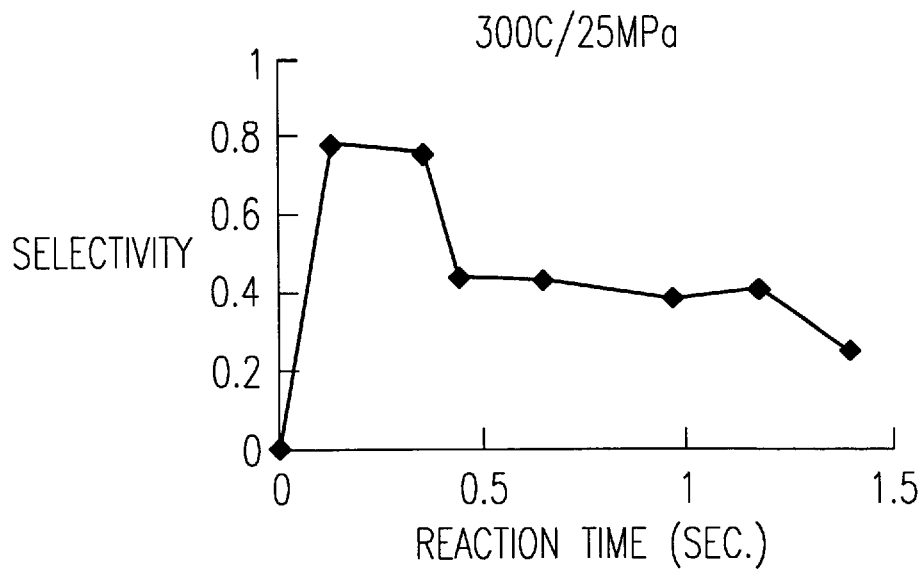
FIGS. 3D and 3E are graphs depicting the relation between the selectivity of erythrose and the reaction time at a sub-critical state (Example 2).
Figure 3E:
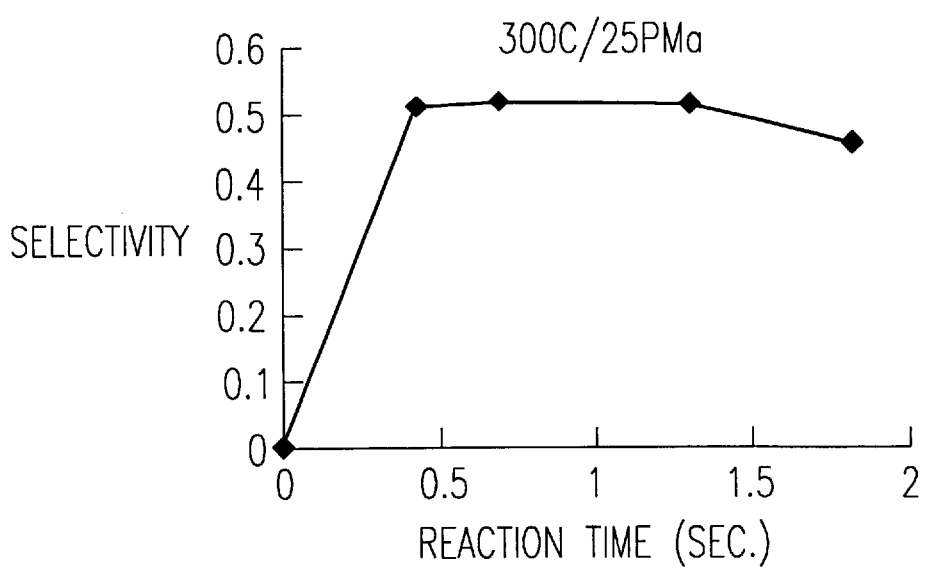

Experiments similar to those as in Example I were carried out under modified temperatures and pressures. The results are shown in FIGS. 3A, 3B, and 3C (at super-critical states) and in FIGS. 3D and 3E (sub-critical states). In the figures, the term "selectivity" means the molar yield of the generated erythrose on the basis of the consumed glucose. It is suggested that if no reduction of the selectivity was observed as the reaction time was prolonged, the generated erythrose could be interpreted as not being decomposed any longer.

These figures show that erythrose can be generated at a super-critical state with a selectivity of 0.6 to 0.8, involving almost no decomposition of the once generated erythrose, even if the pressure and temperature are modified. It is also shown that erythrose can be generated at a sub-critical state with a selectivity of 0.3 to 0.8.

In the present invention, glucose can be selectively transformed readily into erythrose when the decomposition reaction of glucose is carried out in water at a super-critical state or at a sub-critical state, in accordance with the present invention, specifically when the reaction is effected for the reaction time set to a time period with a high generation level of erythrose and a low level of contaminated by-products. The present method thus provides a technique for preparing a highly pure erythrose product from glucose in a high yield and at a high velocity. Japanese patent application JP 112,820/97 is incorporated herein by reference.

What is claimed as new and desired to be secured by Letters Patent of the United State:

1. A method for producing erythrose, comprising 1) decomposing glucose in water at a temperature of 200–800° C. and at a pressure of 2 to 90 MPa, and 2) recovering erythrose produced in 1).

2. A method for producing erythrose according to claim 1, wherein the reaction time of said decomposition is set to a time period where the molar yield of erythrose on the basis of consumed glucose is 0.3 to 0.8.

3. The method of claim 2, wherein said time period is 0.075 to 0.3 sec.

4. The method of claim 2, wherein said time period is 0.15 sec. or more.

5. The method as claimed in claim 2, wherein said molar yeild of erythrose is 0.6 to 0.8.

6. The method as claimed in claim 1, wherein said glucose and water are at a temperature of 300–400° C. and at a pressure of 25–40 Mpa during said decomposition.

7. The method as claimed in claim 1, wherein said glucose is present in said water at a concentration of 0.1 to 10% by weight.

8. The method as claimed in claim 2, wherein said glucose is present in said water at a concentration of 0.1 to 10% by weight.

9. The method as claimed in claim 3, wherein said glucose is present in said water at a concentration of 0.1 to 10% by weight.

10. The method as claimed in claim 4, wherein said glucose is present in said water at a concentration of 0.1 to 10% by weight.

11. The method as claimed in claim 5, wherein said glucose is present in said water at a concentration of 0.1 to 10% by weight.

12. The method as claimed in claim 6, wherein said glucose is present in said water at a concentration of 0.1 to 10% by weight.

13. The method as claimed in claim 9, wherein said glucose and water are at a temperature of 400° C. and a pressure of 30–40 MPa.

14. The method as claimed in claim 13, wherein said glucose is present in said water at a concentration of 0.1 to 10% by weight.

15. The method as claimed in claim 9, wherein said glucose and water are at a temperature of 300–350° C. and a pressure of 25 MPa.

16. The method as claimed in claim 15, wherein said glucose is present in said water at a concentration of 0.1 to 10% by weight.

* * * * *